United States Patent
Ishihara et al.

(10) Patent No.: US 10,832,409 B2
(45) Date of Patent: Nov. 10, 2020

(54) DIAGNOSIS SUPPORT METHOD, DIAGNOSIS SUPPORT APPARATUS, AND NON-TRANSITORY COMPUTER-READABLE STORAGE MEDIUM

(71) Applicant: FUJITSU LIMITED, Kawasaki (JP)

(72) Inventors: Masaki Ishihara, Kawasaki (JP); Ryoichi Funabashi, Kawasaki (JP); Motoo Masui, Inagi (JP); Atsuko Tada, Tokorozawa (JP); Ryuta Tanaka, Machida (JP)

(73) Assignee: FUJITSU LIMITED, Kawasaki (JP)

( * ) Notice: Subject to any disclaimer, the term of this patent is extended or adjusted under 35 U.S.C. 154(b) by 146 days.

(21) Appl. No.: 16/116,232

(22) Filed: Aug. 29, 2018

(65) Prior Publication Data
US 2019/0073772 A1    Mar. 7, 2019

(30) Foreign Application Priority Data
Sep. 1, 2017  (JP) ................................. 2017-168610

(51) Int. Cl.
*G06T 7/00* (2017.01)
*A61B 5/00* (2006.01)
(Continued)

(52) U.S. Cl.
CPC .......... *G06T 7/0014* (2013.01); *A61B 5/4842* (2013.01); *A61B 5/7485* (2013.01);
(Continued)

(58) Field of Classification Search
CPC ...... G06F 19/321; G06F 16/50; G06F 16/583; G06F 3/04817; G06F 19/00;
(Continued)

(56) References Cited

U.S. PATENT DOCUMENTS

2009/0080734 A1   3/2009   Moriya et al.
2010/0226550 A1   9/2010   Miyasa et al.
(Continued)

FOREIGN PATENT DOCUMENTS

JP   2003-325458   11/2003
JP   2007-287018   11/2007
(Continued)

*Primary Examiner* — Golam Sorowar
(74) *Attorney, Agent, or Firm* — Fujitsu Patent Center

(57) ABSTRACT

A diagnosis method performed by a computer includes: executing a process that includes specifying a first case image group which includes one or more case images which have a same abnormality as a first abnormality detected from an image of a subject among plural case images about each of plural patients, each of the plural case images indicating an image in which a progression stage of a disease is different; executing a first selection process that includes calculating a first similarity about a site where the first abnormality appears between each of the one or more case images included in the first case image group and the image of the subject, and selecting a second case image group from the first case image group in accordance with the first similarity with respect to each of the one or more case images included in the first case image group.

19 Claims, 10 Drawing Sheets

(51) Int. Cl.
*G16H 10/60* (2018.01)
*G06T 7/33* (2017.01)
*G06T 7/11* (2017.01)
*G16H 50/70* (2018.01)
*G16H 50/20* (2018.01)
*G16H 30/40* (2018.01)
*A61B 5/08* (2006.01)

(52) U.S. Cl.
CPC .............. *G06T 7/11* (2017.01); *G06T 7/337* (2017.01); *G16H 10/60* (2018.01); *G16H 30/40* (2018.01); *G16H 50/20* (2018.01); *G16H 50/70* (2018.01); *A61B 5/0013* (2013.01); *A61B 5/08* (2013.01); *A61B 2576/00* (2013.01); *G06T 2207/30004* (2013.01)

(58) Field of Classification Search
CPC .... G06F 3/0482; G06F 3/0488; G06F 40/205; G06F 19/36; G06F 40/169; G06F 16/248; G06F 16/245; G06F 19/3418; G06F 16/51; G06F 16/5838; G06F 16/5846; G06F 16/5866; G06F 16/00; G06F 16/24; G06F 2101/00; G06F 16/532; G16H 30/20; G16H 50/70; G16H 10/60; G16H 50/20; G16H 15/00; G16H 30/40; G16H 50/50; G16H 20/10; G16H 10/20; G16H 40/63; G16H 40/67; G16H 70/60; G16H 40/60; G16H 50/30; G16H 30/00; G16H 40/20; G16H 50/00; G16H 70/20; G06T 7/0012; G06T 7/0014; G06T 2207/30004; G06T 2207/30088; G06T 2207/10088; G06T 2207/30068; G06T 2200/24; G06T 2207/30061; G06T 2207/20081; G06T 2207/30016; G06T 11/008; G06T 2207/30008; G06T 2207/30096; G06T 2207/10072; G06T 2207/30052; G06T 7/11; G06T 2207/10081; G06T 2207/10116; G06T 2210/41; G06T 5/40; A61B 5/055; A61B 5/0077; A61B 5/441; A61B 5/7267; A61B 6/032; A61B 10/02; A61B 2034/108; A61B 2090/373; A61B 2090/374; A61B 2090/3762; A61B 2090/378; A61B 34/10; A61B 5/0033; A61B 5/015; A61B 5/0402; A61B 5/4312; A61B 5/444; A61B 5/7246; A61B 5/7425; A61B 5/0075

See application file for complete search history.

(56) References Cited

U.S. PATENT DOCUMENTS

| | | | |
|---|---|---|---|
| 2016/0267221 A1* | 9/2016 | Larcom | G06F 19/321 |
| 2016/0267222 A1* | 9/2016 | Larcom | G06F 19/321 |
| 2016/0335394 A1 | 11/2016 | Kawagishi et al. | |

FOREIGN PATENT DOCUMENTS

| | | |
|---|---|---|
| JP | 2009-223595 | 10/2009 |
| JP | 2010-165127 | 7/2010 |
| JP | 2011-100254 | 5/2011 |
| JP | 2016-214324 | 12/2016 |

* cited by examiner

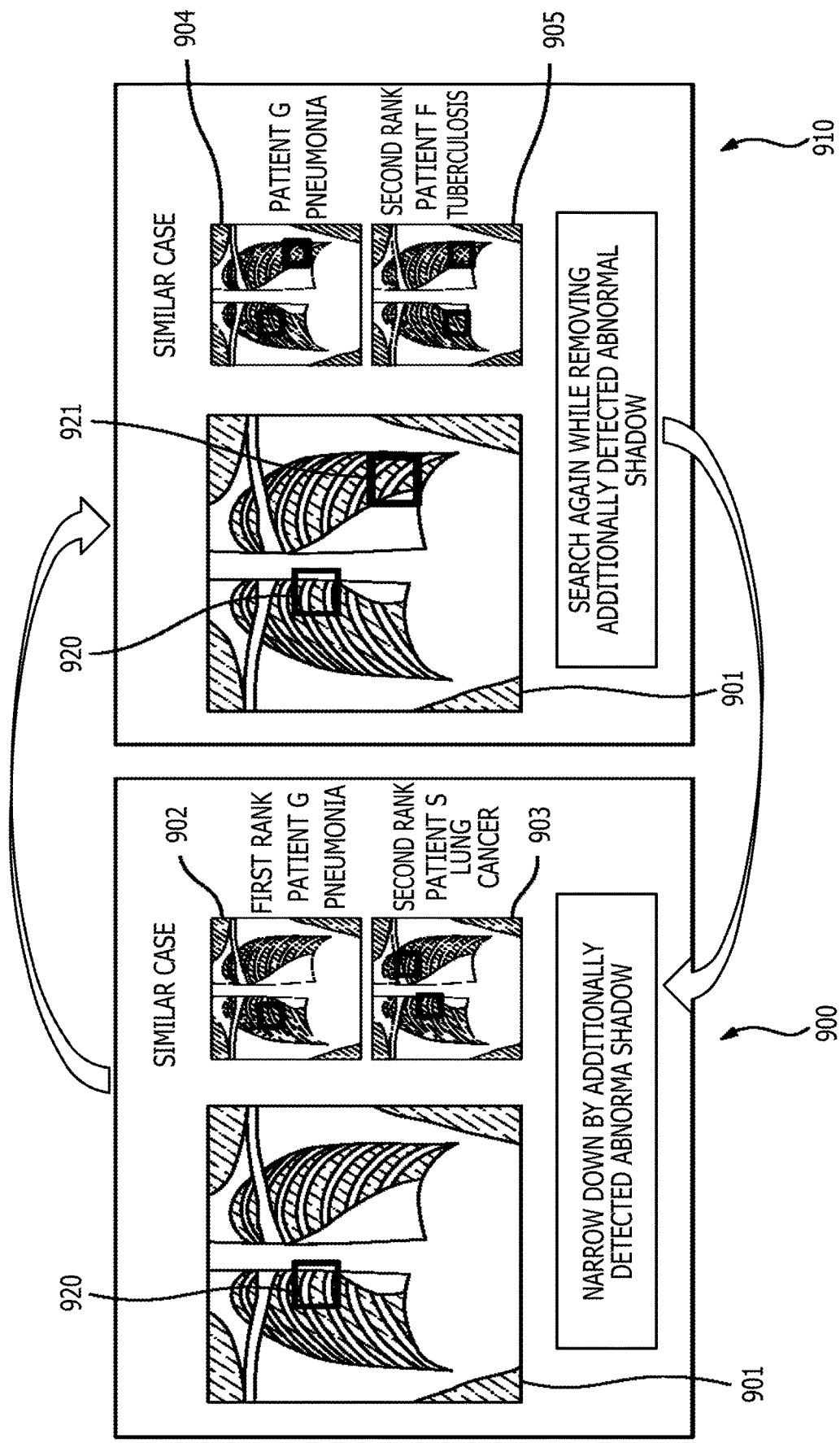

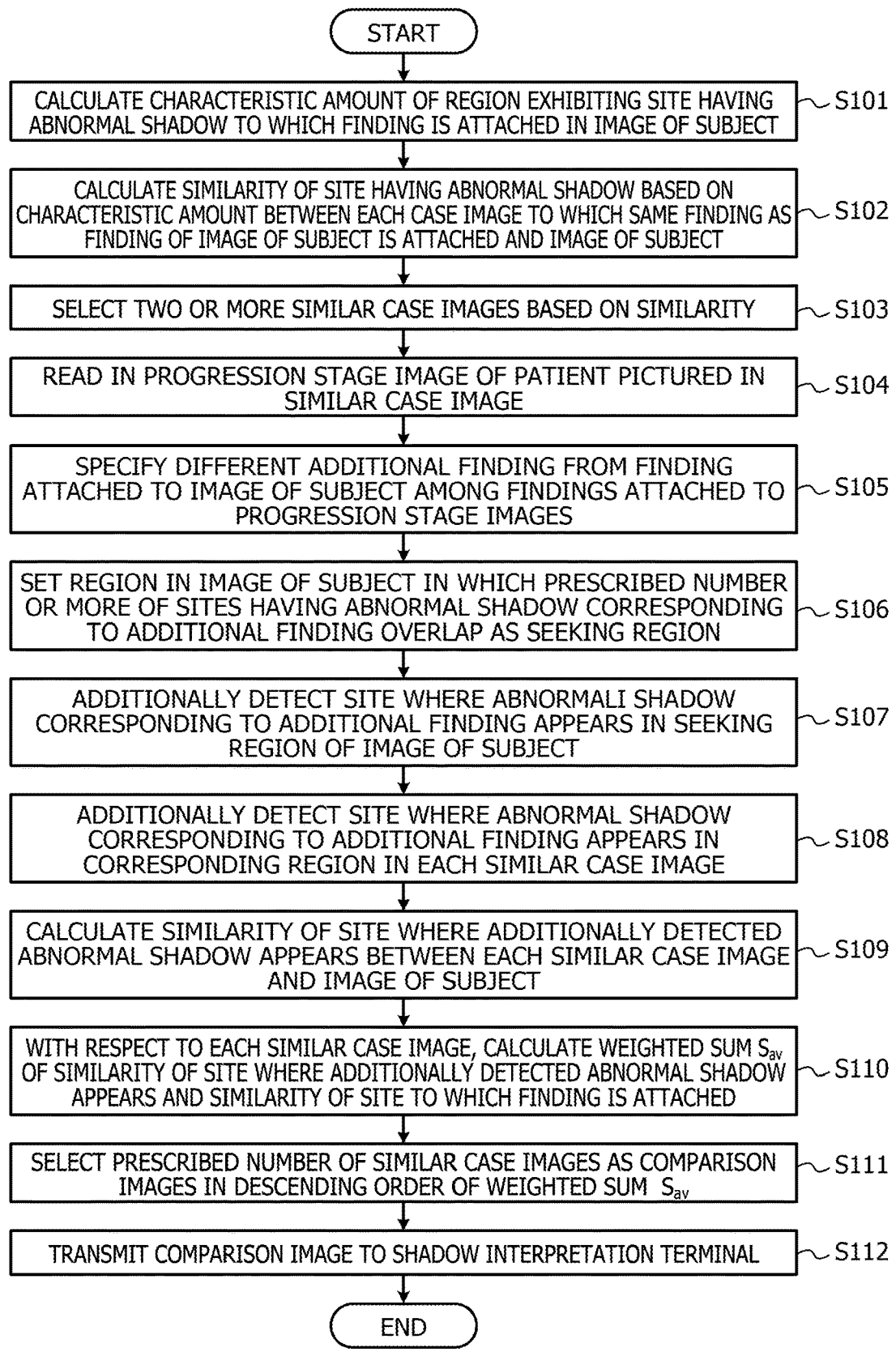

DIAGNOSIS SUPPORT METHOD, DIAGNOSIS SUPPORT APPARATUS, AND NON-TRANSITORY COMPUTER-READABLE STORAGE MEDIUM

CROSS-REFERENCE TO RELATED APPLICATION

This application is based upon and claims the benefit of priority of the prior Japanese Patent Application No. 2017-168610, filed on Sep. 1, 2017, the entire contents of which are incorporated herein by reference.

FIELD

The embodiment discussed herein is related to a diagnosis support method, a diagnosis support apparatus, and a non-transitory computer-readable storage medium for storing a program that support an image diagnosis, for example.

BACKGROUND

In a case where a doctor performs an image diagnosis to specify a disease that a patient possibly contracts (hereinafter, referred to as differential diagnosis) based on an image that is obtained by scanning the patient, an image of another patient may be used as a comparison image. In such a case, in order to appropriately assist the image diagnosis by the doctor, it is desirable to select an image about a disease, in which a similar abnormal shadow to the abnormal shadow represented by a finding by the doctor appears in an image of the patient, as the comparison image. Accordingly, techniques have been suggested which search for an image of another patient which has a similar abnormal shadow to an abnormal shadow detected from an image of a patient. Further, techniques have been suggested which select case data based on the similarity between plural medical images of the same subject which are included in the case data and are scanned in different periods and plural medical image which are scanned for a subject to be an examination target in different periods.

Examples of the related art include Japanese Laid-open Patent Publication No. 2003-325458 and Japanese Laid-open Patent Publication No. 2010-165127.

SUMMARY

According to an aspect of the invention, a diagnosis method performed by a computer includes: executing a process that includes specifying a first case image group which includes one or more case images which have a same abnormality as a first abnormality detected from an image of a subject among plural case images about each of plural patients, each of the plural case images indicating an image in which a progression stage of a disease is different; executing a first selection process that includes calculating a first similarity about a site where the first abnormality appears between each of the one or more case images included in the first case image group and the image of the subject, and selecting a second case image group from the first case image group in accordance with the first similarity with respect to each of the one or more case images included in the first case image group; executing a process that includes specifying a patient of the case image with respect to each of the case images included in the second case image group, specifying another case image which is obtained by scanning later than the case image with respect to the specified patient, and specifying a site where a second abnormality which is different from the first abnormality appears in the case image or the other specified case image; executing an area limitation process that includes specifying a region in the image of the subject in which a prescribed number or more of sites where the second abnormality appears overlap; executing a process that includes detecting the site where the second abnormality appears in the specified region in the image of the subject; and executing a second selection process that includes calculating a second similarity about the site where the second abnormality appears between each of the one or more case images included in the second case image group and the image of the subject, and further selecting the case image from the second case image group in accordance with the second similarity with respect to each of the one or more case images included in the second case image group.

The object and advantages of the invention will be realized and attained by means of the elements and combinations particularly pointed out in the claims.

It is to be understood that both the foregoing general description and the following detailed description are exemplary and explanatory and are not restrictive of the invention, as claimed.

BRIEF DESCRIPTION OF DRAWINGS

FIG. 9 is a diagram that illustrates one example of a display screen of a display device of a shadow interpretation terminal; and FIG. 10 is an action flowchart of the diagnosis support process.

DESCRIPTION OF EMBODIMENT

In the related art, it may be difficult to detect a site that has a characteristic abnormal shadow in an image because the difference is small between the state where such a characteristic abnormal shadow of a disease occurs and a healthy state with respect to a certain site of the human body as in a case where the disease that a patient contracts is in an initial stage. Further, in a case where the site where such an abnormal shadow occurs is not detected in the image of the patient, the site to be used for a search is not specified. Thus, in the above techniques, an appropriate case image may not be searched for.

Meanwhile, in a case where the site where an abnormal shadow occurs is detected from the image of the patient by using a highly sensitive detector in order to detect a slight abnormal shadow, the number of normal sites that are falsely detected as sites where an abnormal shadow occurs (that is, false-positive) may increase. In such a case, if the falsely detected site is used for a search for a similar case image, an image of another patient, which is useful for comparison, may not be selected.

According to an aspect of the present disclosure, provided are diagnosis supporting technologies that may select a suitable image for comparison shadow interpretation for an image of a subject from plural images of various cases.

A diagnosis support device and a diagnosis support method and a diagnosis supporting computer program, which are used in the diagnosis support device, will hereinafter be described with reference to drawings. The diagnosis support device selects an image that is used for comparison shadow interpretation for an image of a patient to be a shadow interpretation target (hereinafter, referred to as subject) from plural images of various cases that are already registered, for example. Note that the image used for the comparison shadow interpretation will hereinafter be referred to simply as comparison image.

In order to select an appropriate number of comparison images, the inventor focused on a fact that even an abnormal shadow, which is difficult to find in an initial stage of a disease, is detected more easily as the stage of the disease progresses more.

Figure 1:
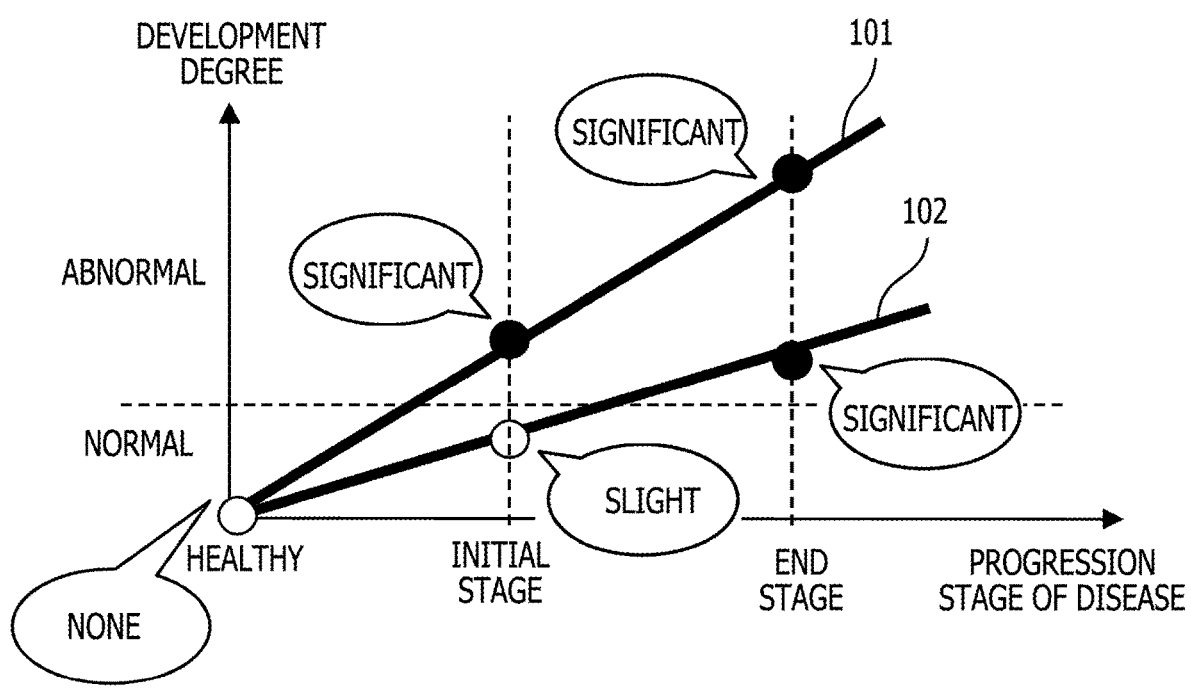
FIG. 1 is a schematic diagram that represents the relationship between a progression stage of a disease and a development degree of an abnormal shadow in the disease.

FIG. 1 is a schematic diagram that represents the relationship between a progression stage of a disease and a development degree of an abnormal shadow in the disease. In FIG. 1, the horizontal axis represents the progression stage of the disease, and the vertical axis represents the development degree of the abnormal shadow. A line 101 and a line 102 respectively represent the relationship between the progression stage of the disease and the development degree of the abnormal shadow with respect to two sites where the abnormal shadow appears in the same disease.

As for the site represented by the line 101, the abnormal shadow significantly appears even in the initial stage of the disease, and the abnormal shadow is thus easily detected in the image. On the other hand, as for the site represented by the line 102, in the initial stage of the disease, the abnormal shadow is slight to the extent that the abnormal shadow may be considered to be normal, and it is thus difficult to detect the abnormal shadow in the image. However, in a case where the disease progresses and becomes an end stage, the abnormal shadow develops in the site represented by the line 102, and it becomes easier to detect the abnormal shadow in the image.

Accordingly, the diagnosis support device selects two or more case images that have a site, which is similar to the site to which a finding is attached in the image of the subject, that is, similar to the site where some sort of abnormal shadow is detected and to which the same finding is attached, from a case image database in which various case images are registered. In a case where, with respect to the respective patients represented by the selected case images, the other case images that are scanned later than the selected case images have a site to which a different finding from the finding attached to the image of the subject is attached, the diagnosis support device specifies the site, that is, specifies the site that has a different abnormal shadow. In addition, the diagnosis support device estimates a region, in which a site where an undetected abnormal shadow occurs is possibly present in the image of the subject, based on the site that has the different abnormal shadow. Further, the diagnosis support device additionally detects a site that has an abnormal shadow in the estimated region and further selects a case image, which has a similar site to the site which is additionally detected and has the abnormal shadow, as the comparison image from the selected two or more case images. Note that herein, an abnormal shadow represents a state where some sort of change such as "lymphadenopathy" or "granular shadow", for example, which is detectable in an image, occurs compared to a healthy state of a site. Further, a finding represents a kind of abnormal shadow, which is attached by a doctor who performs shadow interpretation.

Figure 2:
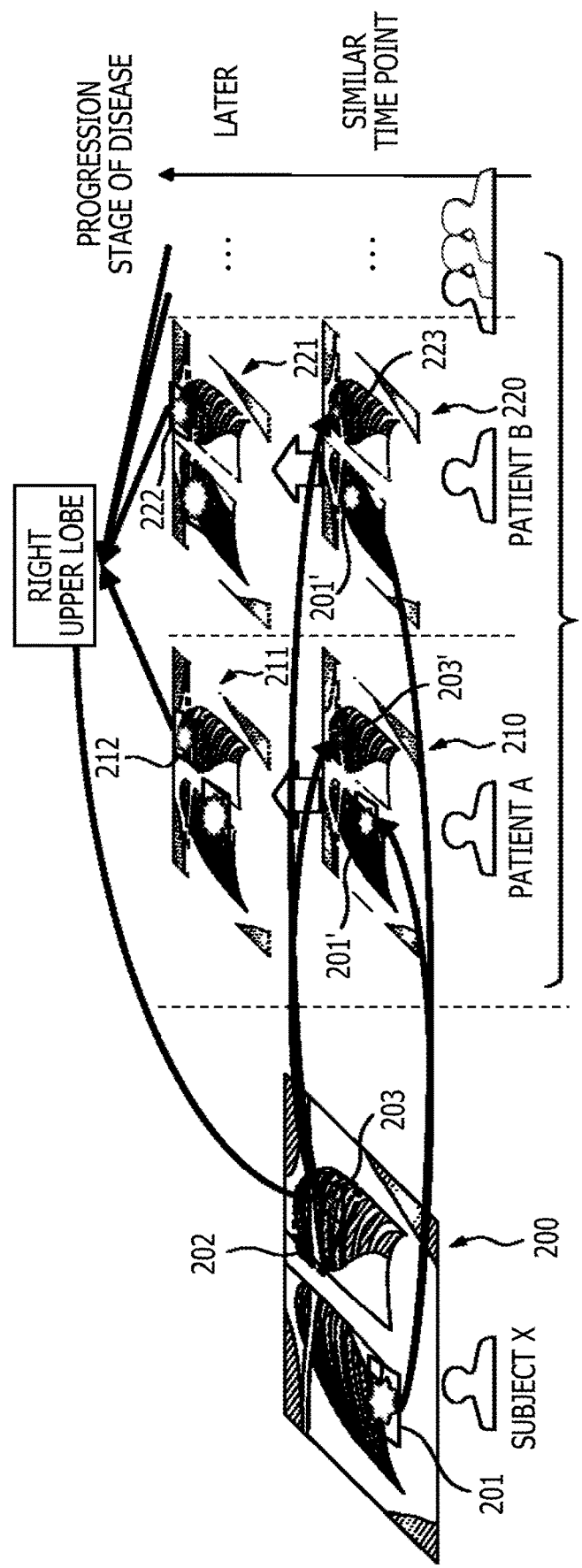
FIG. 2 is a diagram that explains an outline of a diagnosis support process according to this embodiment.

FIG. 2 is a diagram that explains an outline of a diagnosis support process according to this embodiment. In this example, an abnormal shadow is detected with respect to a site 201 in an image 200 of a subject X, and a finding is attached by a doctor. In other words, finding data are registered in a database or the like while being associated with the site 201 in the image 200 of the subject X. In the following, finding data that are associated with a site in a certain case image may be referred to as a finding attached to the case image, a finding attached to a site in the case image, or the like. Further, from the case image database, a case image 210 of a patient A and a case image 220 of a patient B, to whom the same finding as the finding attached to the site 201 is attached (that is, the same abnormal shadow as the abnormal shadow of the site 201 is present) and who have a similar site 201' to the site 201, are selected. Further, the case images of other patients who have the site 201' are similarly selected. Further, with respect to the patient A, in a case image 211 that is scanned later than the time when the case image 210 is scanned and is registered in the case image database, a site 212 to which a different finding from the finding attached to the image 200 is attached is specified. That is, a site where a different abnormal shadow from the abnormal shadow detected in the image 200 appears is specified based on the finding attached to the case image 210. Similarly, with respect to the patient B, in a case image 221 that is scanned later than the time when the case image 220 is scanned and is registered in the case image database, a site 222 to which a different finding from the finding attached to the image 200 is attached is specified. Further, based on the site 212, the site 222, and so forth, a region 202 is estimated which possibly includes a site which has an undetected abnormal shadow in the image 200 of the subject (in this example, the right upper lobe of the lungs). To the estimated region 202, a site 203 where an abnormal shadow that corresponds to the finding attached to the site 212 or the finding attached to the site 222 appears is additionally detected. Further, from the selected case images, the case image 210, which has the same abnormal shadow as the abnormal shadow in the additionally detected site 203 and has a similar site 203' to the site 203, is further selected as the comparison image. Meanwhile, although a site 223 where an abnormal shadow appears in a region that corresponds to the region 202 is additionally detected in the case image 220, the similarity between the site 223 and the site 203 is low. Thus, the case image 220 is not selected. Then, the case image 210 is displayed for the comparison shadow interpretation.

Figure 3:
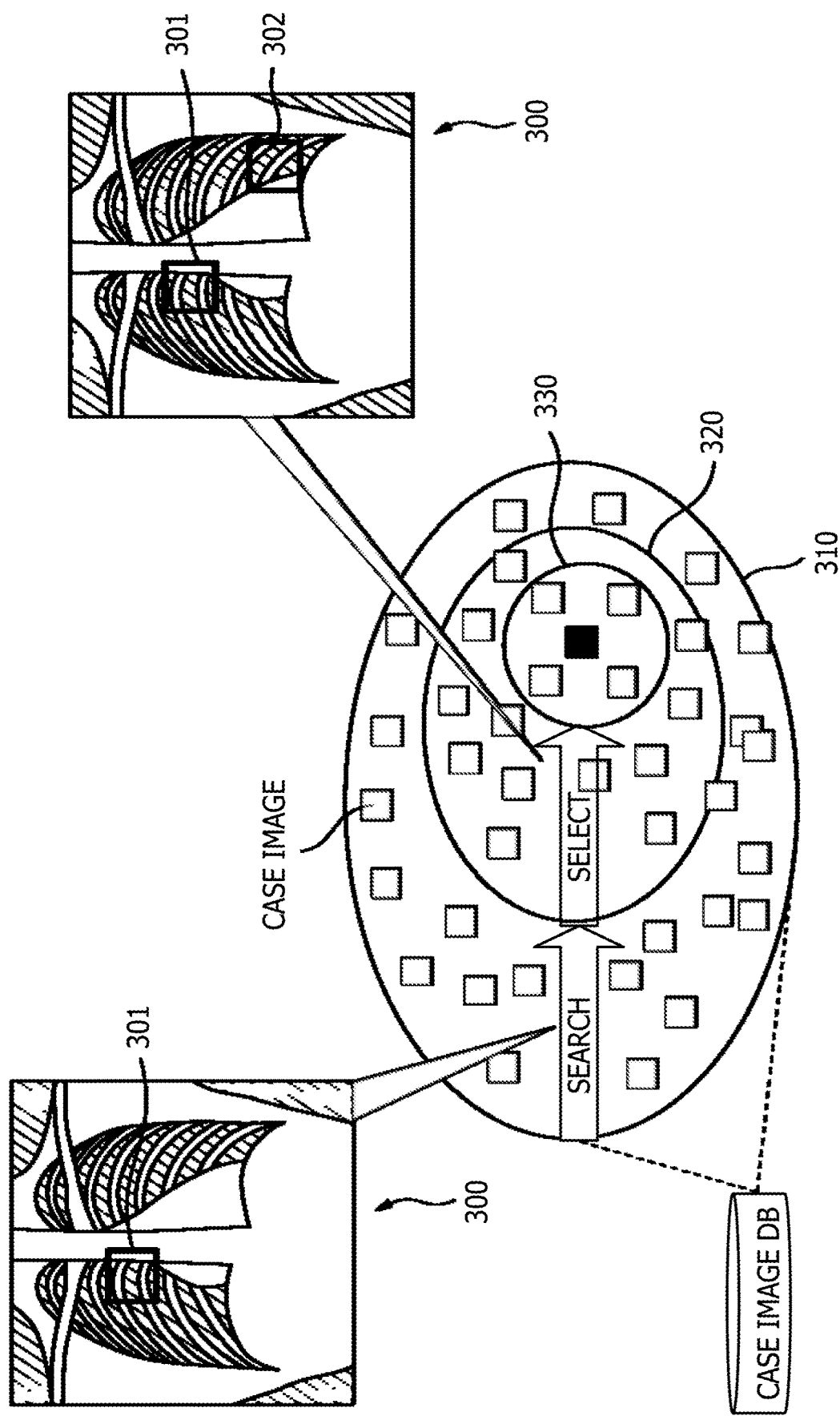
FIG. 3 is a diagram that illustrates one example of the relationship between a comparison image selected by the diagnosis support process according to this embodiment and a case image selected based on a finding attached to an image of a subject.

FIG. 3 is a diagram that illustrates one example of the relationship between the comparison image selected by the diagnosis support process according to this embodiment and the case image selected based on the finding attached to the image of the subject. For example, many case images are included in a set 320 of case images, which is searched for from a set 310 of case images which is registered in the case image database based on one finding attached to an image 300 of the subject, that is, one detected abnormal shadow 301. Many case images of different diseases from the disease of the subject are included in the many case images included in the set 320. Meanwhile, in the image 300 of the subject, the case image is further selected from the set 310 based on an abnormal shadow 302 that is additionally detected as described above together with the abnormal shadow 301, and a set 330 may thereby be obtained. Thus, the number of case images included in the set 330 is less than the number of case images included in the set 320. As a result, many of the case images of different diseases from the disease of the subject are not included in the set 320. In such a manner, in this embodiment, appropriate case images for the comparison shadow interpretation are selected.

Note that images and case images in this embodiment may be images that are generated by any of various kinds of modality such as an X-ray image-capturing device or a computer tomography image-capturing device, for example, or may be images that are obtained by applying some sort of process to the images. Further, in this embodiment, a value of a pixel of an image and a case image may be a density, luminance, a modality specific value, or a value defined by a standard of a format of a medical image, for example.

Figure 4:
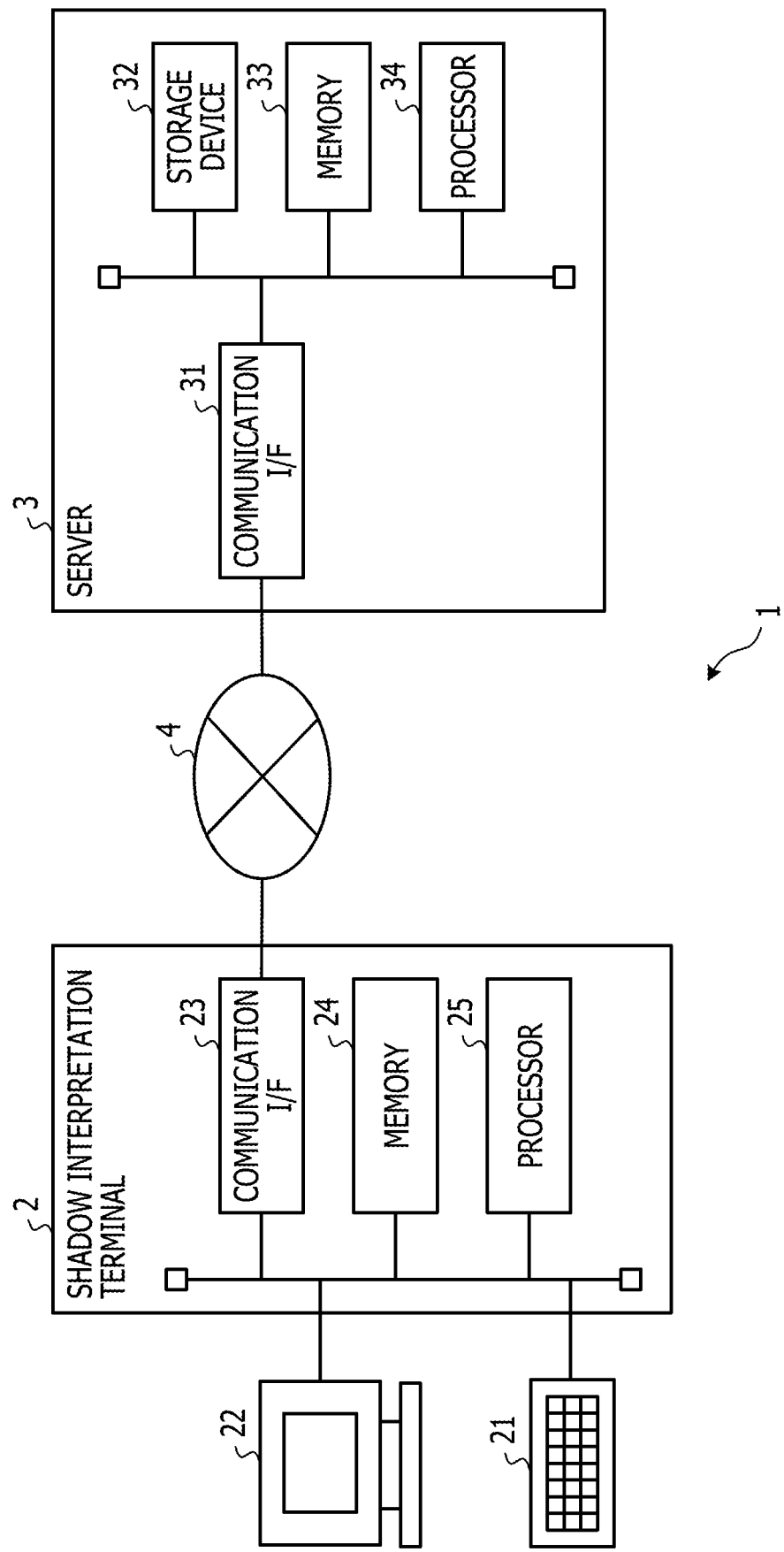
FIG. 4 is an overview configuration diagram of a diagnosis support system.

FIG. 4 is an overview configuration diagram of a diagnosis support system that includes the diagnosis support device according to this embodiment. A diagnosis support system 1 may be a system that complies with picture archiving and communication systems (PACS), for example, and has a shadow interpretation terminal 2 and a server 3, and the shadow interpretation terminal 2 and the server 3 are capable of mutual communication via a communication network 4. Note that plural shadow interpretation terminals 2 that are provided to the diagnosis support system 1 may be present. Similarly, plural servers 3 that are provided to the diagnosis support system 1 may be present. Further, the communication network 4 may be a communication network that complies with any of various communication standards, for example, Ethernet®.

The shadow interpretation terminal 2 is a terminal that is used by a doctor for performing shadow interpretation in an image of a subject and has an input apparatus 21, a display device 22, a communication interface 23, a memory 24, and a processor 25. The shadow interpretation terminal 2 may further have a storage device (not illustrated) such as a magnetic recording device. Further, the processor 25 is connected with the other portions of the shadow interpretation terminal 2 by a signal line, for example.

The input apparatus 21 has an apparatus for operating the shadow interpretation terminal 2 such as a keyboard or a mouse, for example. Further, the input apparatus 21 generates an operation signal corresponding to an operation by a doctor and outputs the operation signal to the processor 25.

The display device 22 has a liquid crystal display or an organic EL display, for example, and displays an image or the like accepted from the processor 25. Note that the input apparatus 21 and the display device 22 may integrally be formed as a touch panel display, for example.

The communication interface 23 has an interface for connecting the shadow interpretation terminal 2 with the communication network 4, a control circuit for communication, and so forth. Further, the communication interface 23 transmits various kinds of signals, which are accepted from the processor 25 and are transmitted to the server 3, for example, a signal, which includes an image of a subject, a finding about the image, and information which indicates a site to which a finding is attached, to the server 3 via the communication network 4. Further, the communication interface 23 receives an image of a subject from any of various kinds of modality or the server 3 via the communication network 4 and passes the received image to the processor 25. In addition, the communication interface 23 receives various kinds of signals, for example, the comparison image or the like from the server 3 via the communication network 4 and passes the received signal to the processor 25.

The memory 24 has a volatile and readable and writable semiconductor memory, for example. The memory 24 may further have a non-volatile and read-only semiconductor memory. Further, the memory 24 temporarily saves an image of a subject, a finding about an image of a subject, information that indicates a site to which a finding is attached, a comparison image, and so forth, for example.

The processor 25 has a central processing unit (CPU) and peripheral circuits thereof, for example. In addition, the processor 25 may have a processor for numerical value computation or a graphical processing unit (GPU). Further, the processor 25 controls the whole shadow interpretation terminal 2. Further, the processor 25 saves an image of a subject and the comparison image, which are accepted from the other apparatus such as the server 3, for example, in the memory 24 and causes the display device 22 to display the image of the subject and the comparison image. Further, the processor 25 saves a finding about an image of a subject and information indicating a site to which a finding is attached, which are input by the input apparatus 21, in the memory 24 while associating the finding and the information with the image of the subject. In addition, the processor 25 generates a signal that includes an image of a subject, a finding about the image, and information which indicates a site to which a finding is attached and transmits the generated signal to the server 3 via the communication interface 23 and the communication network 4.

The server 3 is one example of the diagnosis support device and has a communication interface 31, a storage device 32, a memory 33, and a processor 34, for example. The server 3 may further have an input apparatus (not illustrated) such as a keyboard and a display device (not illustrated). Further, the processor 34 is connected with the other portions of the server 3 by a signal line, for example.

The communication interface 31 has an interface for connecting the server 3 with the communication network 4, a control circuit for communication, and so forth. Further, the communication interface 31 passes a signal, which is received from the shadow interpretation terminal 2 via the communication network 4 and includes an image of a subject, a finding, and information which indicates a site to which a finding is attached, to the processor 34. Further, the communication interface 31 transmits the comparison image or the like accepted from the processor 34 to the shadow interpretation terminal 2 via the communication network 4.

The storage device 32 is one example of a storage unit and has at least any of a magnetic disk recording device and an optical recording device, for example. Further, the storage device 32 stores the case image database in which plural case images of various cases are registered. In this embodiment, a definitive diagnosis is performed for a patient that is represented by each of the case images registered in the case image database. Further, with respect to each of the case images, the name of the patient who is pictured in the case image and the name of the disease, a finding about the case image, and information that indicates the site to which the finding is attached (that is, the site where an abnormal shadow is detected) are associated together and stored. In addition, with respect to each of the case images, a characteristic amount of a region in which the site to which the finding is attached in the case image is exhibited is also stored while being associated with the case image. The characteristic amount may be local binary pattern (LBP), histograms of oriented gradients (HOG), edge orientation histograms (EOH), or values themselves of pixels of the region in which the site to which the finding is attached is exhibited, for example. Those characteristic amounts may be extracted by the processor 34 of the server 3 in a case where the case image is registered in the case image database, for example. Note that the finding that is attached to an individual case image is not limited to one finding but may be plural findings. In a case where plural findings are attached, the characteristic amount may be extracted with respect to each site to which the finding is attached and may be stored together with the case image. Further, in the case image database, plural case images, which are scanned such that, with respect to an individual patient, a substantially same site is pictured at different timings, are registered. Note that to each of plural case images about the same patient, for example, information by which the scanning order such as a scanning date or a progression stage of a disease is understood is attached.

In addition, the storage device 32 may store a computer program for the diagnosis support process.

The memory 33 is another example of the storage unit and has a volatile and readable and writable semiconductor memory, for example. The memory 33 may further have a non-volatile and read-only semiconductor memory. Further, the memory 33 stores a computer program for the diagnosis support process, which is read out from the storage device 32, during execution of the diagnosis support process, for example. In addition, the memory 33 temporarily saves an image of a subject, a finding about an image of a subject, information that indicates a site to which a finding is attached, various kinds of data that are generated during execution of the diagnosis support process, and so forth.

The processor 34 is one example of a control unit and has a central processing unit (CPU) and peripheral circuits thereof, for example. In addition, the processor 34 may have a processor for numerical value computation. Further, the processor 34 controls the whole server 3. Further, the processor 34 executes the diagnosis support process. Further, the processor 34 selects a prescribed number of comparison images from the plural case images registered in the case image database and transmits the selected comparison images to the shadow interpretation terminal 2 via the communication interface 31 and the communication network 4.

Figure 5:
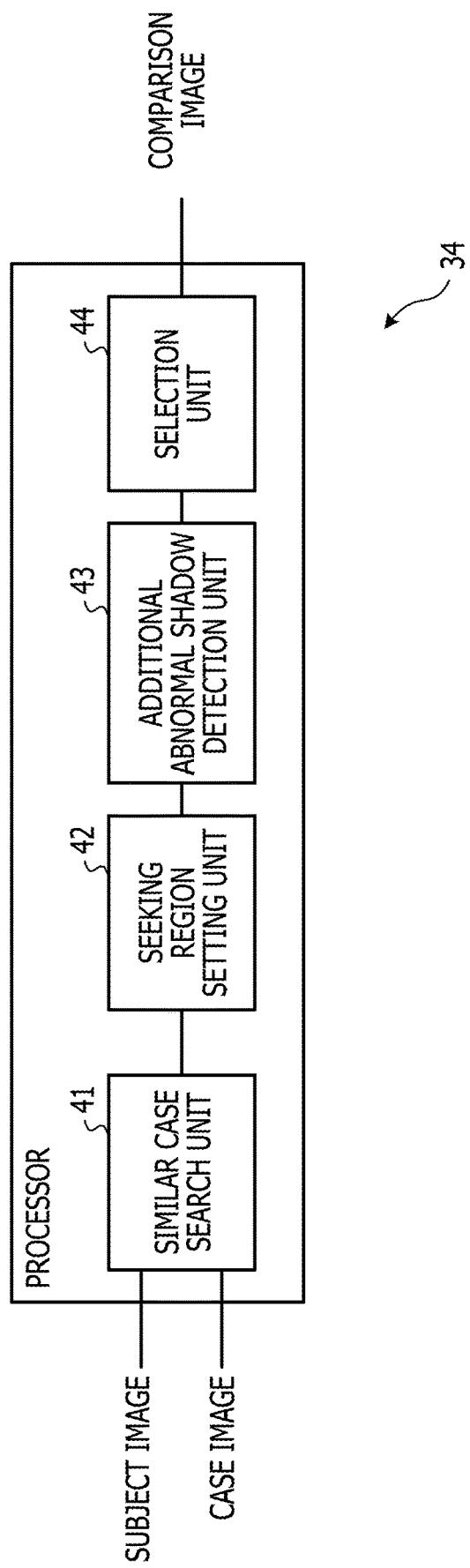
FIG. 5 is a function block diagram of a processor provided to a sever, which is related to the diagnosis support process.

FIG. 5 is a function block diagram of the processor 34, which is related to the diagnosis support process. The processor 34 has a similar case search unit 41, a seeking region setting unit 42, an additional abnormal shadow detection unit 43, and a selection unit 44.

Those units provided to the processor 34 are function modules that are realized by a computer program executed on the processor 34, for example. Alternatively, those units may be implemented as dedicated computation circuits that are implemented in a portion of the processor 34.

The similar case search unit 41 selects two or more case images, in which the same abnormal shadow as the abnormal shadow detected from the image of the subject is detected and the site where the abnormal shadow appears is similar to the site where the abnormal shadow appears in the image of the subject, from the plural case images registered in the case image database. In other words, the similar case search unit 41 specifies one or more case images (which may be referred to as first case image group), in which the same abnormal shadow as the abnormal shadow (which may be referred to as first abnormal shadow) detected from the image of the subject is detected, from the plural case images registered in the case image database. Further, the similar case search unit 41 calculates the similarity (which may be referred to as first similarity) about the site where the first abnormal shadow appears between each of one or more case images included in the first case image group and the image of the subject. In addition, the similar case search unit 41 selects a second case image group from the first case image group in accordance with the first similarity. Here, the second case image group are correspondent to two or more case images, in which the same abnormal shadow as the abnormal shadow detected from the image of the subject is detected and the site where the abnormal shadow appears is similar to the site where the abnormal shadow appears in the image of the subject.

In order to determine the degree of similarity, the similar case search unit 41 extracts the characteristic amount of the region in which the site to which the finding is attached is exhibited in the image of the subject. The characteristic amount is the same kind of characteristic amount as the characteristic amount, which is extracted from the case image registered in the case image database, and may be LBP, HOG, EOH, or the region itself in which the site to which the finding is attached is exhibited, for example.

The similar case search unit 41 specifies and reads in the case images, to which the same finding as the finding attached to the image of the subject is attached, that is, the case images (which may be referred to as first case image group), in which the same abnormal shadow as the abnormal shadow detected from the image of the subject is detected, from the plural case images registered in the case image database. Further, with respect to each of the case images that are read in, the similar case search unit 41 calculates the similarity of the site where the same abnormal shadow is detected between the case image and the image of the subject. In this case, the similar case search unit 41 may calculate the similarity by using the characteristic amount of the region in the case image that includes the site to which the finding is attached and the characteristic amount of the region in the image of the subject. For example, in a case where the characteristic amount is represented by a bit string like LBP, the similar case search unit 41 may calculate, as the similarity, the reciprocal number of a value (HD+α), which is a value resulting from addition of an offset value a (for example, α=1) to a hamming distance HD between the two characteristic amounts as similarity calculation targets. Alternatively, the similar case search unit 41 may calculate, as the similarity, the reciprocal number of a value (D+α), which is a value resulting from addition of the offset value a to a Euclidean distance D between the two characteristic amounts as the similarity calculation targets. Further, in a case where the values themselves of the pixels of the region in which the site to which the finding is attached is exhibited are used as the characteristic amount, the similar case search unit 41 may calculate, as the similarity, the normalized cross-correlation value between the two characteristic amounts as the similarity calculation targets.

The similar case search unit 41 selects a prescribed number of case images as the similar case images (which may be referred to as second case image group) in descending order of the similarity. The prescribed number may be 10 to 100, for example. Alternatively, the similar case search unit 41 may select the case image that has the similarity which is equal to or more than a prescribed threshold value as the similar case image. The prescribed threshold value may be a value that results from multiplication of the maximum value, which the value of the similarity may take, by 0.5 to 0.7, for example.

Note that plural findings may be attached to the image of the subject, that is, plural abnormalities may be detected from the image of the subject. In such a case, the similar case search unit 41 specifies and reads in the case images, to which the same finding as any of the plural findings attached to the image of the subject is attached, that is, the case images, in which the same abnormal shadow as any of the abnormalities detected from the image of the subject is detected, from the case image database. Further, with respect to each of the case images that are read in, the similar case search unit 41 may calculate a similarity S in accordance with the following formula.

$$S = r \sum_{i=1}^{n} S_i / n \quad (1)$$

Here, n represents the number of abnormalities that match any of the plural abnormalities detected from the image of the subject among one or more abnormalities detected from the case image. $S_i$ represents the similarity about the ith abnormal shadow among the abnormalities that match between the case image and the image of the subject. Further, a coefficient r is the ratio of the number of abnormalities that match between the selected case image and the image of the subject to the number of abnormalities detected from the image of the subject. For example, in a case where the number of abnormalities detected from the image of the subject is 3 and the number of abnormalities that match between the selected case image and the image of the subject is 1, r=⅓ is obtained. Further, in a case where the number of abnormalities detected from the image of the subject is 3 and the number of abnormalities that match between the selected case image and the image of the subject is 3, r=1 is obtained. The similarity is calculated in such a manner, and the similar case search unit 41 may thereby make the case image, in which the number of abnormalities matching the plural abnormalities detected from the image of the subject is more, be more easily selected as the similar case image. Thus, the case image of a patient who has the same disease as the disease of the subject is more easily selected as the similar case image.

The plural case images selected as the similar case images (which may be referred to as second case image group) may include two or more case images of the same patient. In this case, the similar case search unit 41 may leave only the primary case image among the two or more case images of the same patient as the similar case image and may remove the other case images than the primary case image from the similar case images. Alternatively, the similar case search unit 41 may leave only the case image whose similarity is the maximum among the two or more case images of the same patient as the similar case image and may remove the other case images than the case image whose similarity is the maximum from the similar case images. Still alternatively, the similar case search unit 41 may set each of the two or more case images of the same patient as the similar case image.

The similar case search unit 41 saves the selected similar case images and the similarities calculated for the similar case images in the memory 33.

The seeking region setting unit 42 specifies the patient who is pictured in the similar case image with respect to each of the similar case images. With respect to each of the specified patients, the seeking region setting unit 42 reads in the case image, which is scanned later than the similar case image of the patient, (which will hereinafter be referred to as progression stage image for convenience of description) from the case image database. With respect to each of the progression stage images, the seeking region setting unit 42 sets the finding, which is not attached to the image of the subject, among the findings attached to the progression stage image as an additional finding. That is, an abnormal shadow that is indicated by the additional finding is a different abnormal shadow from the abnormal shadow detected in the image of the subject.

Figure 6:
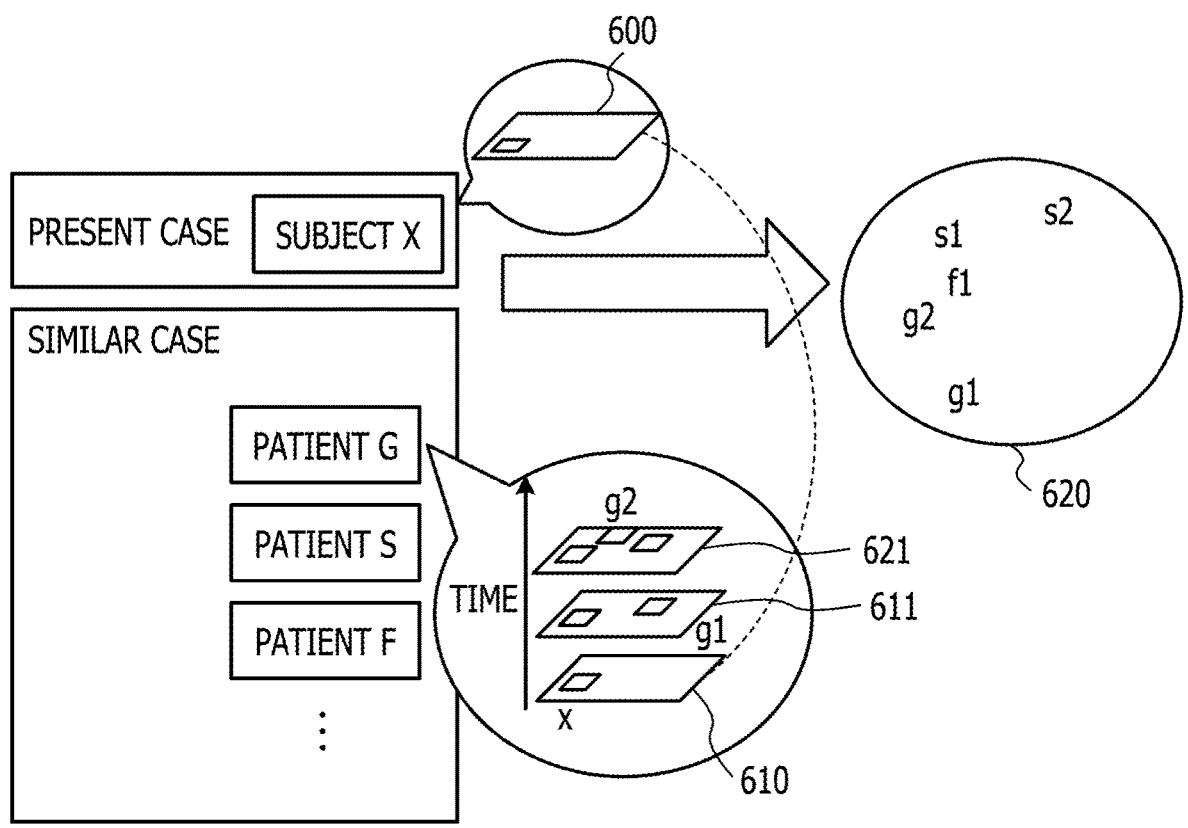
FIG. 6 is a diagram that explains an outline of additional finding detection.

FIG. 6 is a diagram that explains an outline of additional finding detection. In this example, a finding x is attached in an image 600 of the subject X. Further, the case images of a patient G, a patient S, a patient F, and so forth are selected as the similar case images. Among those, to progression stage images 611 and 612 that are scanned for the patient G later than a similar case image 610 about the patient G, findings g1 and g2 that are not attached to the image 600 are respectively attached. Accordingly, the findings g1 and g2 are set as the additional findings. In this example, similarly, additional findings f1, s1, and s2 are respectively detected from the progression stage images of the other patient S, patient F, and so forth. Further, a set 620 of the additional findings are used for setting of a seeking region.

The seeking region setting unit 42 specifies a region in the image of the subject, in which a prescribed number (for example, 3 to 5) or more of sites where the abnormalities indicated by the additional findings appear overlap, as the seeking region.

For example, in a case where, with respect to each of the progression stage images, the region that includes the site to which the finding is attached is indicated in the progression stage image, the seeking region setting unit 42 aligns each of the progression stage images that have the additional findings with the image of the subject. Note that in general, even the same site has a different shape and size in each patient. Further, the position and shape of the site in the image change due to positioning or the like in scanning. Accordingly, the seeking region setting unit 42 may align each of the progression stage images with the image of the subject by using a non-rigid registration method, for example, such that the same sites match each other. Note that the seeking region setting unit 42 may align each of the progression stage images with the image of the subject by using another alignment method.

With respect to each of the aligned progression stage images, the seeking region setting unit 42 casts a vote of '1' to each pixel in the region that includes the site to which the additional finding is attached. Then, the seeking region setting unit 42 may calculate the sum of vote values for each pixel and may set the set of the pixels for which the sum becomes a prescribed number or more as the seeking region.

Figure 7:
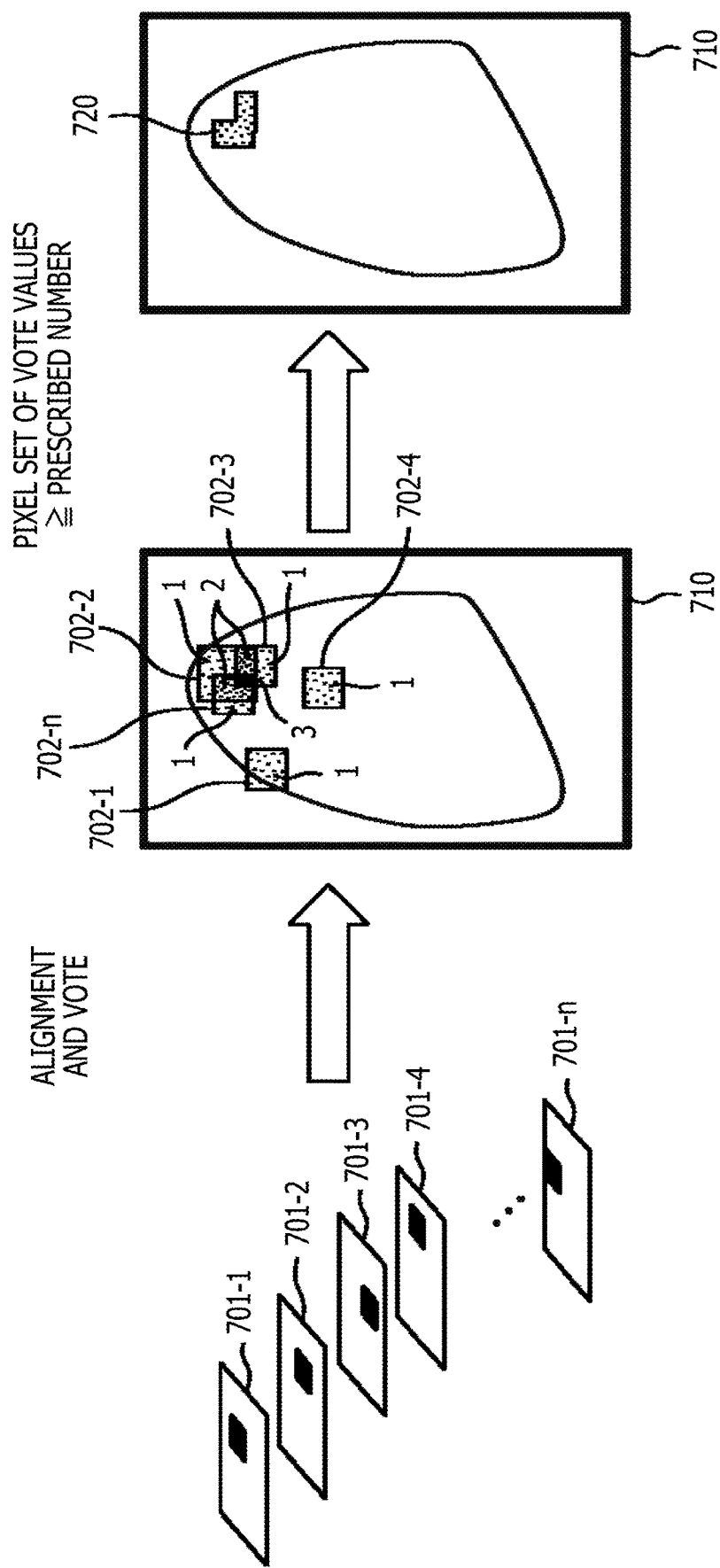
FIG. 7 is an explanatory diagram of an outline of seeking region setting.

FIG. 7 is an explanatory diagram of an outline of seeking region setting. Each of progression stage images 701-1 to 701-n is aligned with an image 710 of the subject. Then, in the image 710, with respect to each of regions 702-1 to 702-n that include the sites to which the additional findings are attached in the aligned progression stage images 701-1 to 701-n, a vote of '1' is casted to each pixel included in the region. Then, the set of pixels for which the sum of the vote values becomes a prescribed number or more in the image 710 is set as a seeking region 720.

In a modification example, with respect to each of the progression stage images, the site to which the finding is attached may be described by a text. In such a case, the seeking region setting unit 42 detects a description that represents the name of the site from the description of the additional finding of the progression stage image with respect to each of the progression stage images and casts a vote of '1' to the site that corresponds to the name detected in an anatomical site model in which sites are hierarchically described. In this example, with respect to each site, text data of the name of the site are in advance stored in the memory 33. Then, in a case where the portion that matches the text data of the name of any site among the descriptions of the additional findings is present, the seeking region setting unit 42 may set the site that corresponds to the matched text data as the site to which the additional finding is attached. Further, in a case where a site as a lower layer of the detected site is present in the anatomical site model, the seeking region setting unit 42 casts a vote of '1' to the site as the lower layer.

The seeking region setting unit 42 calculates the sum of the vote values for each of the sites and specifies the site for which the sum of the vote values becomes a prescribed number or more in the anatomical site model. Then, the seeking region setting unit 42 aligns a reference image, which represents an image model of the sites of a standard human body, with the image of the subject by using the non-rigid registration method such that the same sites match each other. Note that the seeking region setting unit 42 may align the reference image with the image of the subject by using another alignment method. Then, the seeking region setting unit 42 sets the region that exhibits the specified site in the aligned reference image in the image of the subject as the seeking region.

Figure 8:
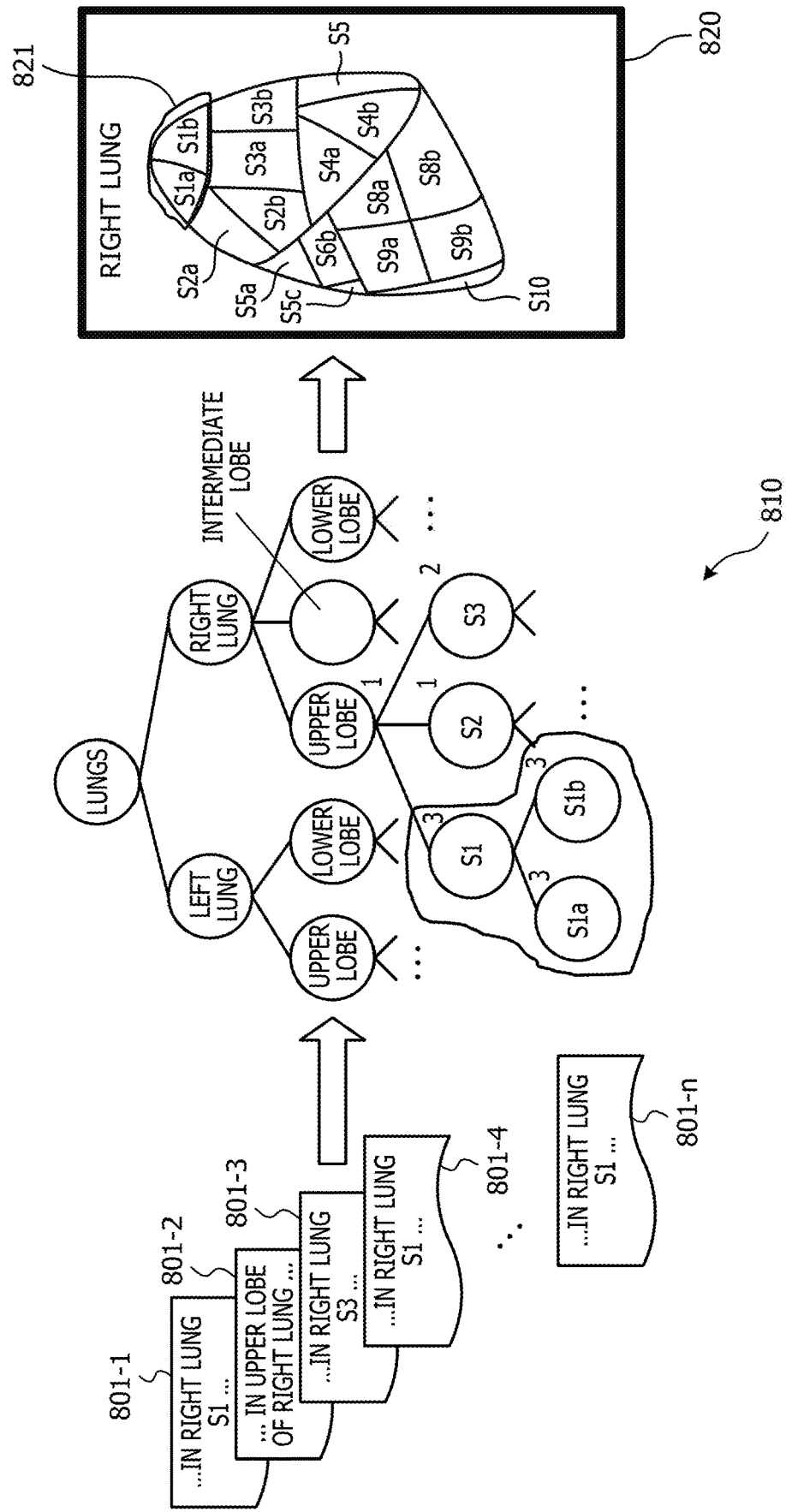
FIG. 8 is an explanatory diagram of an outline of the seeking region setting according to a modification example.

FIG. 8 is an explanatory diagram of an outline of the seeking region setting according to this modification example. The names of the sites to which the additional findings are attached are respectively detected from descriptions 801-1 to 801-n of the additional findings. For example, "right lung S1." is detected as the name of the site to which the additional finding is attached from the description 801-1 of the additional finding. Similarly, "upper lobe of right lung" is detected as the name of the site to which the additional finding is attached from the description 801-2 of the additional finding. Then, in an anatomical site model 810, a vote of '1' is casted to the site that corresponds to the detected name for each of the names of the additional findings. Note that "S1a" and "S1b" as the lower layers of "right lung S1." detected from the description 801-1 are included in the anatomical site model 810. Thus, in a case where a vote is casted to "right lung S1", votes are also casted to "S1a" and "S1b". Similarly, "right lung S1", "S1a", and "S1b" as the lower layers of "upper lobe of right lung" detected from the description 801-2 are included in the anatomical site model 810. Thus, in a case where a vote is casted to "upper lobe of right lung", votes are also casted to "right lung S1", "S1a", and "S1b". Further, for example, in a case where the sum of the vote values becomes a prescribed number or more for "right lung S1", the region that is correspondent to "right lung S1" in the reference image which is aligned with the image 820 of the subject is set as a seeking region 821 in the image 820.

Note that an image model itself that is represented by the reference image may represent the anatomical site model. In this case, it is sufficient that in the image model, with respect to each site, the relationships between the sites of upper layers and the sites of lower layers of the site concerned are provided.

The seeking region setting unit 42 may further set the seeking region for each of the similar case images. In this case, the seeking region setting unit 42 may align the similar case image with the image of the subject similarly to the alignment between the reference image and the image of the subject and may set the region that corresponds to the seeking region in the image of the subject in the aligned similar case image as the seeking region in the similar case image.

The seeking region setting unit 42 notifies the additional abnormal shadow detection unit 43 of the set seeking region with respect to each of the image of the subject and the similar case images.

The additional abnormal shadow detection unit 43 detects the site, in which the abnormal shadow indicated by the additional finding in any of the progression stage images appears, in the seeking region in the image of the subject. For example, with respect to each of the additional findings included in the seeking region, the additional abnormal shadow detection unit 43 detects the site where the abnormal shadow appears from the seeking region by using a detector that in advance performs learning for detection of the abnormal shadow which corresponds to the additional finding. In this case, the additional abnormal shadow detection unit 43 sets a window in the seeking region, for example, and calculates the characteristic amount (for example, LBP or HOG) to be input to the detector from the value of each pixel in the window. The additional abnormal shadow detection unit 43 inputs the characteristic amount to the detector and thereby assesses whether or not an abnormal shadow is present in the site included in the window. The additional abnormal shadow detection unit 43 repeats the above process while changing the position of the window and may thereby detect an abnormal shadow even in a case where the abnormal shadow is present in the site pictured in any position in the seeking region. As the detector, the additional abnormal shadow detection unit 43 may use a detector based on AdaBoost, a support vector machine, multilayer perceptron, or the like, for example.

The additional abnormal shadow detection unit 43 sets the region, which corresponds to the window in a case where an abnormal shadow is detected, as the region that includes the site where the detected abnormal shadow occurs. In such a manner, the additional abnormal shadow detection unit 43 additionally detects an abnormal shadow only in the seeking region and may thereby inhibit false detection of an abnormal shadow outside the seeking region (that is, detection of a false-positive site). Thus, as the detector, the additional abnormal shadow detection unit 43 may use a detector that is adjusted so as to be unlikely to fail to detect an actual abnormal shadow although likely to falsely detect an abnormal shadow. For example, the detector may be adjusted such that, in an ROC curve that represents the relationship between detection sensitivity and a false-positive rate, the detection sensitivity is higher than the detection sensitivity in the closest position to a left upper end and the false-positive rate becomes high.

Similarly, with respect to each of the similar case images, the additional abnormal shadow detection unit 43 detects the site where an abnormal shadow appears from the seeking region of each of the similar case images and specifies the region that includes the site.

With respect to each of the image of the subject and the similar case images, the additional abnormal shadow detection unit 43 notifies the selection unit 44 of the site where the additionally detected abnormal shadow occurs and the region that includes the site.

The selection unit 44 calculates the characteristic amount such as LBP, HOG, or EOH from the region that includes the site where the additionally detected abnormal shadow occurs in the image of the subject. Similarly, with respect to each of the similar case images, the selection unit 44 calculates the characteristic amount from the region that includes the site where the additionally detected abnormal shadow occurs. Note that the selection unit 44 may not calculate the characteristic amount for the similar case images in which an abnormal shadow is not additionally detected.

The selection unit 44 calculates the similarity of the site where the additionally detected abnormal shadow occurs between each of the similar case images and the image of the subject. In this case, similarly to the similar case search unit 41, the selection unit 44 may calculate the similarity based on the hamming distance, the Euclidean distance, or the normalized cross-correlation value between the characteristic amounts calculated from the region that includes the site where the additionally detected abnormal shadow occurs. Note that the selection unit 44 may set the similarity to zero for the similar case images in which an abnormal shadow is not additionally detected.

With respect to each of the similar case images, the selection unit 44 calculates a weighted sum $S_{av}$ of the similarity calculated by the similar case search unit 41 (that is, the similarity about the site to which the finding is attached by the doctor) and the similarity about the site where the additionally detected abnormal shadow occurs, in accordance with the following formula.

$$S_{av}=(a \cdot S1+b \cdot S2)/(a+b) \qquad (2)$$

Here, S1 is the similarity about the site to which the finding is attached by the doctor, and S2 is the similarity about the site where the additionally detected abnormal shadow occurs. a and b are weighting coefficients and are set as a=0.5 and b=0.5, for example. Note that in a case where the site where the additionally detected abnormal shadow occurs is focused, the weighting coefficients may be set as a=0.3 and b=0.7 such that b becomes larger than a. Particularly, the weighting coefficients may be set such that a=0 and b=1. In this case, the similarity about the site to which the finding is attached by the doctor is not referred to, but the comparison image is selected. Conversely, in a case where the site to which the finding is attached by the doctor is focused more than the site where the additionally detected abnormal shadow occurs, the weighting coefficients may be set as a=0.7 and b=0.3 such that a becomes larger than b.

The selection unit 44 selects a prescribed number of images as the comparison images from the similar case images in descending order of the weighted sum $S_{av}$. Note that in a case where plural case images of the same patient are included in the selected comparison images, the selection unit 44 may set only the case image for which the weighted sum $S_{av}$ is the maximum among the plural case images of the same patient as the comparison image. Note that the prescribed number may be 1 to 10, for example. Alternatively, the selection unit 44 may select the similar case image that has the weighted sum $S_{av}$ which is equal to or more than a prescribed threshold value as the comparison image.

The selection unit 44 transmits each of the selected comparison images, information that indicates the region which includes the site where additionally detected abnormal shadow occurs in each of the comparison images, kinds of abnormalities that are additionally detected, and the weight sums $S_{av}$ to the shadow interpretation terminal 2. In addition, the selection unit 44 transmits information that indicates the region which includes the site where the additionally detected abnormal shadow occurs in the image of the subject and kinds of abnormalities that are additionally detected to the shadow interpretation terminal 2.

In a case where the processor 25 of the shadow interpretation terminal 2 receives the comparison image from the server 3, the processor 25 causes the display device 22 to display the received comparison image together with the image of the subject. In this case, the processor 25 may cause the display device 22 to display one or two comparison images, which are selected by the doctor via the input apparatus 21, among the received comparison images. That is, the comparison images to be displayed may be switched in response to the operation by the doctor. Further, in response to the operation by the doctor via the input apparatus 21, the processor 25 may cause the display device 22 to further display the information that indicate the region which includes the site where the additionally detected abnormal shadow occurs and the kinds of abnormalities for both or either one of the image of the subject and the displayed comparison image. Alternatively, the information that indicates the region in which the site where the additionally detected abnormal shadow occurs is exhibited may not be displayed. Furthermore, in response to the operation by the doctor, the processor 25 may switch whether to display the comparison image selected based on the additionally detected abnormal shadow or to display the selected similar case image without using the additionally detected abnormal shadow. In a case where the similar case image is displayed, the processor 25 transmits a signal to request the similar case image to the server 3 via the communication interface 23. Then, in a case where the processor 34 of the server 3 receives the signal, the processor 34 may transmit the similar case images that are selected by the similar case search unit 41 to the shadow interpretation terminal 2.

FIG. 9 is a diagram that illustrates one example of a display screen of the display device 22 of the shadow interpretation terminal 2. In a screen 900, two similar case images 902 and 903 in descending order of the similarity are displayed together with an image 901 of the subject. Note that a reference numeral 920 that indicates the site to which the finding is attached by the doctor is indicated in each image. Further, by the operation by the doctor, as an image 910, comparison images 904 and 905 that are further selected from the similar case images by referring to the additionally detected abnormal shadow are displayed together with the image 901 of the subject. Further, in this case, not only the reference numeral 920 that indicates the site to which the finding is attached by the doctor but also a reference numeral 921 that indicates the additionally detected site is indicated.

FIG. 10 is an action flowchart of the diagnosis support process according to this embodiment. The processor 34 of the server 3 may execute the diagnosis support process in accordance with the following action flowchart at each time when the image of the subject is accepted from the shadow interpretation terminal 2.

The similar case search unit 41 calculates the characteristic amount from the region that includes the site to which the finding is attached by the doctor (that is, the site where the abnormal shadow is detected) in the image of the subject (step S101). The similar case search unit 41 reads in the case images that have the same finding as the finding attached to the image of the subject from the case image database. Then, based on the characteristic amount, the similar case search unit 41 calculates the similarity of the site where the same abnormal shadow is detected between each of the case images, which are read out, and the image of the subject (step S102). In addition, based on the similarity, the similar case search unit 41 selects two or more case images as the similar case images from the case images that are read out (step S103).

The seeking region setting unit 42 specifies the patient who is pictured in the similar case image with respect to each of the similar case images and reads in the progression stage image from the case image database with respect to each of the specified patients (step S104). Then, with respect to each of the progression stage images, the seeking region setting unit 42 sets the finding, which is not attached to the image of the subject, among the findings attached to the progression stage image as the additional finding (step S105). Then, the seeking region setting unit 42 sets the region in the image of the subject, in which a prescribed number or more of sites where the abnormalities indicated by the additional findings appear overlap, as the seeking region (step S106). In addition, in each of the similar case images, the seeking region setting unit 42 sets the region that corresponds to the seeking region in the image of the subject as the seeking region in the similar case image.

The additional abnormal shadow detection unit 43 additionally detects the site, in which the abnormal shadow appears, in the seeking region in the image of the subject (step S107). In addition, the additional abnormal shadow detection unit 43 additionally detects the site, in which the abnormal shadow appears, in the seeking region in the similar case image with respect to each of the similar case images (step S108).

The selection unit 44 calculates the similarity of the site where the additionally detected abnormal shadow appears between each of the similar case images and the image of the subject (step S109). Then, with respect to each of the similar case images, the selection unit 44 calculates the weighted sum $S_{av}$ of the similarity about the site where the additionally detected abnormal shadow appears and the similarity about the site to which the finding is attached by the doctor (step S110). Then, the selection unit 44 selects a prescribed number of similar case images as the comparison images from the similar case images in descending order of the weighted sum $S_{av}$ (step S111). The selection unit 44 transmits the selected comparison images and so forth to the shadow interpretation terminal 2 in order to cause the display device 22 of the shadow interpretation terminal 2 to display the selected comparison images and so forth (step S112). Then, the processor 34 finishes the diagnosis support process.

As described in the above, the diagnosis support device selects the similar case images that have the site, which is similar to the site to which the finding is attached in the image of the subject and to which the same finding is attached, from the case image database. With respect to each of the selected similar case images, the diagnosis support device sets the seeking region, which possibly includes an undetected abnormal shadow in the image of the subject, in accordance with the other finding attached to the progression stage image that is later scanned for the patient who is pictured in the similar case image. In addition, the diagnosis support device detects the site, in which the abnormal shadow appears, in the seeking region in the image of the subject and detects the site, in which the abnormal shadow appears, also in the corresponding region in each of the similar case images. Further, the diagnosis support device calculates the similarity of the site where the additionally detected abnormal shadow appears between the image of the subject and each of the similar case images and selects the comparison image from the similar case images based on the similarity. Thus, the diagnosis support device may select an appropriate comparison image even in a case where an appropriate comparison image may not be selected from the finding by the doctor because an abnormal shadow which is difficult to find is present in the image of the subject. As a result, the diagnosis support device may assist the doctor in performing an appropriate differential diagnosis. Further, an appropriate differential diagnosis is performed, and performance of an undesired examination for the subject may thereby be avoided, or an examination to be performed for the subject may thereby be selected appropriately.

In a modification example, the similar case search unit 41 may read in not only the case image, to which the same finding as the finding attached to the image of the subject is attached, but also the case image, to which a similar finding is attached, as a selection target of the similar case image from the case image database. For example, in a case where the abnormal shadow about each of two findings may be considered to be the same, the two findings are mutually similar. Also with respect to the case image to which a similar finding is attached, the similar case search unit 41 calculates the similarity between the site to which the finding is attached in the image of the subject and the site to which the similar finding is attached. Further, similarly to the above embodiment, the similar case search unit 41 may assess whether or not the case image to which the similar finding is attached is selected as the similar case image in accordance with the similarity. In this case, for example, a reference table that indicates combinations of mutually similar findings is in advance stored in the memory 33. Then, the processor 34 may refer to the reference table and may thereby specify the similar finding to the finding attached to the image of the subject.

In this modification example, the similar case search unit 41 may select the similar case image also from the case image in which the same kind of abnormal shadow as the abnormal shadow detected from the image of the subject is detected but to which a different finding from the finding attached to the image of the subject is attached.

Further, in another modification example, in a case where a site where a different abnormal shadow from the abnormal shadow detected from the image of the subject is detected is present in the selected similar case image, the seeking region setting unit 42 may use the site for setting of the seeking region similarly to the site where the abnormal shadow is detected in the progression stage image. Accordingly, even in a case where the case image of another patient at a progression stage that progresses more than the progression stage of the disease of the subject is selected as the similar case image, the seeking region setting unit 42 may appropriately specify the site to use for setting of the seeking region and may thus set the seeking region appropriately.

Further, in this modification example, with respect to the similar case image in which the site where the different abnormal shadow from the abnormal shadow detected from the image of the subject is detected is included in the seeking region, the additional abnormal shadow detection unit 43 may not execute a detection process of an additional abnormal shadow from the seeking region.

In still another modification example, the diagnosis support device may be implemented in a stand-alone device. For example, the storage device provided to the shadow interpretation terminal 2 may store the case image database, and the processor 25 of the shadow interpretation terminal 2 may execute a process of each portion of the diagnosis support process. Further, a server that stores the case image database may be provided separately from a server or a shadow interpretation terminal that executes the diagnosis support process. Further, the server or the shadow interpretation terminal that executes the diagnosis support process may read in the case image from the server that stores the case image database via the communication network.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiment of the present invention has been described in detail, it should be understood that the various changes, substitutions, and alterations could be made hereto without departing from the spirit and scope of the invention.

What is claimed is:

1. A diagnosis method performed by a computer, the method comprising:
   executing a process that includes
      obtaining a first case image group from among plural case images about each of plural patients, the first case image group including one or more case images, each of the one or more case images included in the first case image group having a same abnormality as a first abnormality detected from an image of a subject, each of the plural case images indicating an image in which a progression stage of a disease is different;
   executing a first selection process that includes
      calculating a first similarity about a first site where the first abnormality appears between each of the one or more case images included in the first case image group and the image of the subject, and
      obtaining a second case image group from the first case image group in accordance with the first similarity with respect to each of the one or more case images included in the first case image group;
   executing a process that includes
      obtaining a patient of the case image with respect to each of the case images included in the second case image group,
      obtaining another case image which is obtained by scanning later than the case image with respect to the patient, and
      for each patient in the second case image group, obtaining a second site associated with information indicating a second abnormality different from the first abnormality, the obtaining of the second site being performed by using any of the case image and the other case image with respect to each patient in the second case image group;
   executing an area limitation process that includes obtaining a region in the image of the subject, the obtained region being a region corresponding to an area in which a prescribed number or more of second sites each associated with the information indicating the second abnormality are overlapped with each other by the obtaining of the second site for each patient;
   executing a process that includes detecting a third site where the second abnormality appears in the obtained region in the image of the subject; and
   executing a second selection process that includes
      calculating, for each of the one or more case images included in the second case image group, a second similarity between the second site and the third site by using the second case image group and the image of the subject, and
      selecting the case image from the second case image group in accordance with the second similarity with respect to each of the one or more case images included in the second case image group.

2. The diagnosis method according to claim 1, the method comprising:
   executing a process that includes causing a display device to display the case image selected by the second selection process and the image of the subject.

3. The diagnosis method according to claim 1, wherein the area limitation process includes aligning each of the case images in which the second abnormality is detected with the image of the subject, and
   the obtaining of the region is performed by using the aligned case images.

4. The diagnosis method according to claim 1, wherein the area limitation process includes
   by specifying a region in a reference image that represents a model of a human body which is correspondent to the second site associated with the information indicating the second abnormality with respect to each of the case images in which the second abnormality is detected, obtaining a reference region that is correspondent to the prescribed number or more of second sites which overlap in the reference image, and
   aligning the reference image with the image of the subject to specify a region in the image of the subject that is correspondent to the reference region as a region in the image of the subject in which the prescribed number or more of second sites each associated with the information indicating the second abnormality are overlapped.

5. The diagnosis method according to claim 4, wherein the obtaining of the reference region includes
   detecting a name of the second site associated with the information indicating the second abnormality from a description about a finding that is associated with the case image with respect to each of the case images in which the second abnormality is detected, and
   specifying a region in the reference image that is correspondent to the second site associated with the information indicating the second abnormality based on the detected name of the second site.

6. The diagnosis method according to claim 1, the method further comprising:
   executing a process that includes detecting the second site associated with the information indicating the second abnormality in a region in the case image which corresponds to the obtained region in the image of the subject with respect to the case image in which the second abnormality is not detected among the two or more selected case images.

7. The diagnosis method according to claim 1, wherein the calculating of the first similarity includes
   making the first similarity higher for the case image in which the number of same abnormalities as plural abnormalities detected from the image of the subject is more among the plural specified case images in a case where the plural abnormalities detected from the image of the subject are present.

8. A diagnosis support apparatus comprising:
   a memory; and a processor coupled to the memory and configured to
execute a process that includes
obtaining a first case image group from among plural
case images about each of plural patients, the first
case image group including one or more case
images, each of the one or more case images
included in the first case image group having a same
abnormality as a first abnormality detected from an
image of a subject, each of the plural case images
indicating an image in which a progression stage of
a disease is different;
execute a first selection process that includes
calculating a first similarity about a first site where the
first abnormality appears between each of the one or
more case images included in the first case image
group and the image of the subject, and
obtaining a second case image group from the first case
image group in accordance with the first similarity
with respect to each of the one or more case images
included in the first case image group;
execute a process that includes
obtaining a patient of the case image with respect to
each of the case images included in the second case
image group,
obtaining another case image which is obtained by
scanning later than the case image with respect to the
patient, and
for each patient in the second case image group,
obtaining a second site associated with information
indicating a second abnormality different from the
first abnormality, the obtaining of the second site
being performed by using any of the case image and
the other case image with respect to each patient in
the second case image group;
execute an area limitation process that includes obtaining
a region in the image of the subject, the obtained region
being a region corresponding to an area in which a
prescribed number or more of second sites each asso-
ciated with the information indicating the second
abnormality are overlapped with each other by the
obtaining of the second site for each patient;
execute a process that includes detecting a third site where
the second abnormality appears in the obtained region
in the image of the subject; and
execute a second selection process that includes
calculating, for each of the one or more case images
included in the second case image group, a second
similarity between the second site and the third site
by using the second case image group and the image
of the subject, and
selecting the case image from the second case image
group in accordance with the second similarity with
respect to each of the one or more case images
included in the second case image group.

9. The diagnosis support apparatus according to claim 8,
wherein the process is further configured to
execute a process that includes causing a display device to
display the case image selected by the second selection
process and the image of the subject.

10. The diagnosis support apparatus according to claim 8,
wherein
the area limitation process includes
aligning each of the case images in which the second
abnormality is detected with the image of the sub-
ject, and
the obtaining of the region is performed by using the
aligned case images.

11. The diagnosis support apparatus according to claim 8,
wherein
the area limitation process includes
by specifying a region in a reference image that rep-
resents a model of a human body which is corre-
spondent to the second site associated with the
information indicating the second abnormality with
respect to each of the case images in which the
second abnormality is detected, obtaining a reference
region that is correspondent to the prescribed number
or more of second sites which overlap in the refer-
ence image, and
aligning the reference image with the image of the
subject to specify a region in the image of the subject
that is correspondent to the reference region as a
region in the image of the subject in which the
prescribed number or more of second sites each
associated with the information indicating the sec-
ond abnormality are overlapped.

12. The diagnosis support apparatus according to claim
11, wherein
the obtaining of the reference region includes
detecting a name of the second site associated with the
information indicating the second abnormality from
a description about a finding that is associated with
the case image with respect to each of the case
images in which the second abnormality is detected,
and
specifying a region in the reference image that is
correspondent to the second site associated with the
information indicating the second abnormality based
on the detected name of the second site.

13. A non-transitory computer-readable storage medium
for storing a diagnosis program that causes a processor to
execute processing for route search, the processing compris-
ing:
executing a process that includes
obtaining a first case image group from among plural
case images about each of plural patients, the first
case image group including one or more case
images, each of the one or more case images
included in the first case image group having a same
abnormality as a first abnormality detected from an
image of a subject, each of the plural case images
indicating an image in which a progression stage of
a disease is different;
executing a first selection process that includes
calculating a first similarity about a first site where the
first abnormality appears between each of the one or
more case images included in the first case image
group and the image of the subject, and
obtaining a second case image group from the first case
image group in accordance with the first similarity
with respect to each of the one or more case images
included in the first case image group;
executing a process that includes
obtaining a patient of the case image with respect to
each of the case images included in the second case
image group,
obtaining another case image which is obtained by
scanning later than the case image with respect to the
patient, and
for each patient in the second case image group,
obtaining a second site associated with information
indicating a second abnormality different from the
first abnormality, the obtaining of the second site
being performed by using any of the case image and the other case image with respect to each patient in the second case image group;

executing an area limitation process that includes obtaining a region in the image of the subject, the obtained region being a region corresponding to an area in which a prescribed number or more of second sites each associated with the information indicating the second abnormality are overlapped with each other by the obtaining of the second site for each patient;

executing a process that includes detecting a third site where the second abnormality appears in the obtained region in the image of the subject; and executing a second selection process that includes
calculating, for each of the one or more case images included in the second case image group, a second similarity between the second site and the third site by using the second case image group and the image of the subject, and
selecting the case image from the second case image group in accordance with the second similarity with respect to each of the one or more case images included in the second case image group.

14. The non-transitory computer-readable storage medium according to claim 13,
wherein the processing further includes
executing a process that includes causing a display device to display the case image selected by the second selection process and the image of the subject.

15. The non-transitory computer-readable storage medium according to claim 13, wherein
the area limitation process includes
aligning each of the case images in which the second abnormality is detected with the image of the subject, and
the obtaining of the region is performed by using the aligned case images.

16. The non-transitory computer-readable storage medium according to claim 13, wherein
the area limitation process includes
by specifying a region in a reference image that represents a model of a human body which is correspondent to the second site associated with the information indicating the second abnormality with respect to each of the case images in which the second abnormality is detected, obtaining a reference region that is correspondent to the prescribed number or more of second sites which overlap in the reference image, and
aligning the reference image with the image of the subject to specify a region in the image of the subject that is correspondent to the reference region as a region in the image of the subject in which the prescribed number or more of second sites each associated with the information indicating the second abnormality are overlapped.

17. The non-transitory computer-readable storage medium according to claim 16, wherein
the obtaining of the reference region includes
detecting a name of the second site associated with the information indicating the second abnormality from a description about a finding that is associated with the case image with respect to each of the case images in which the second abnormality is detected, and
specifying a region in the reference image that is correspondent to the second site associated with the information indicating the second abnormality based on the detected name of the second site.

18. The non-transitory computer-readable storage medium according to claim 13,
wherein the processing further includes
executing a process that includes detecting the second site associated with the information indicating the second abnormality in a region in the case image which corresponds to the obtained region in the image of the subject with respect to the case image in which the second abnormality is not detected among the two or more selected case images.

19. The non-transitory computer-readable storage medium according to claim 13, wherein
the calculating of the first similarity includes making the first similarity higher for the case image in which the number of same abnormalities as plural abnormalities detected from the image of the subject is more among the plural specified case images in a case where the plural abnormalities detected from the image of the subject are present.

* * * * *